United States Patent
Lee et al.

(10) Patent No.: US 10,045,926 B2
(45) Date of Patent: Aug. 14, 2018

(54) METHOD FOR SKIN WHITENING USING CHEMOKINE

(71) Applicant: Amorepacific Corporation, Seoul (KR)

(72) Inventors: Eun Kyung Lee, Yongin-si (KR); Ji Yeon Han, Yongin-si (KR); Eun Gyung Cho, Yongin-si (KR); Tae Ryong Lee, Yongin-si (KR); Hyun Jung Choi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/329,316

(22) PCT Filed: Jul. 24, 2015

(86) PCT No.: PCT/KR2015/007721
§ 371 (c)(1),
(2) Date: Jan. 26, 2017

(87) PCT Pub. No.: WO2016/018001
PCT Pub. Date: Feb. 4, 2016

(65) Prior Publication Data
US 2017/0209358 A1    Jul. 27, 2017

(30) Foreign Application Priority Data
Jul. 31, 2014 (KR) .......................... 10-2014-0098395

(51) Int. Cl.
*A61Q 19/02* (2006.01)
*A61K 38/19* (2006.01)
*A61K 8/64* (2006.01)

(52) U.S. Cl.
CPC ............... *A61K 8/64* (2013.01); *A61K 38/19* (2013.01); *A61Q 19/02* (2013.01)

(58) Field of Classification Search
None
See application file for complete search history.

(56) References Cited

FOREIGN PATENT DOCUMENTS

| KR | 10-2013-0056955 A | 5/2013 |
|---|---|---|
| WO | 02/059301 A1 | 8/2002 |
| WO | 2004/005892 A2 | 1/2004 |

OTHER PUBLICATIONS

Katherine E. Cole, et al., "Interferon-inducible T Cell Alpha Chemoattractant (I-TAC): A Novel Non-ELR CXC Chemokine with Potent Activity on Activated T Cells through Selective High Affinity Binding to CXCR3", J. Exp. Med., Jun. 15, 1998, pp. 2009-2021, vol. 187, No. 12.

Karkada Mohan, et al., "IFN-γ-Inducible T Cell α Chemoattractant Is a Potent Stimulator of Normal Human Blood T Lymphocyte Transendothelial Migration: Differential Regulation by IFN-γ and TNF-α", J. Immunol., Jun. 15, 2002, pp. 6420-6428, vol. 168, No. 12.

(Continued)

*Primary Examiner* — Kevin S Orwig
(74) *Attorney, Agent, or Firm* — Sughrue Mion, PLLC

(57) ABSTRACT

The present invention relates to a composition containing a chemokine, particularly, an interferon-inducible T-cell alpha chemoattractant (ITACT) which can decrease the gene expression of a factor related to melanin pigment production in melanocytes, thereby exhibiting a skin whitening effect.

7 Claims, 3 Drawing Sheets

(56) References Cited

OTHER PUBLICATIONS

Claire Q.F. Wang, et al., "IL-17 and TNF Synergistically Modulate Cytokine Expression while Suppressing Melanogenesis: Potential Relevance to Psoriasis", J. Invest. Dermatol, 2013, pp. 2741-2752. vol. 133, No. 12.
International Searching Authority, International Search Report of PCT/KR2015/007721, dated Nov. 17, 2015. [PCT/ISA/210].

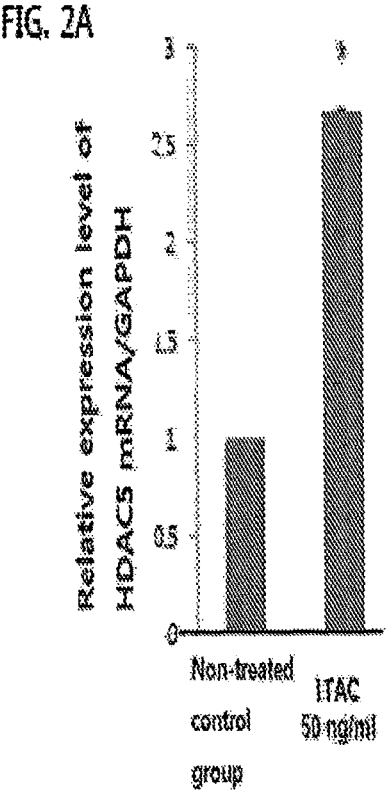
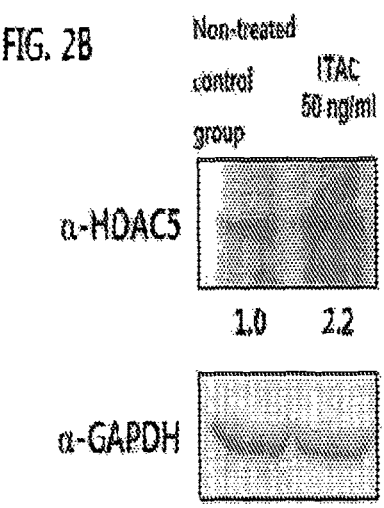
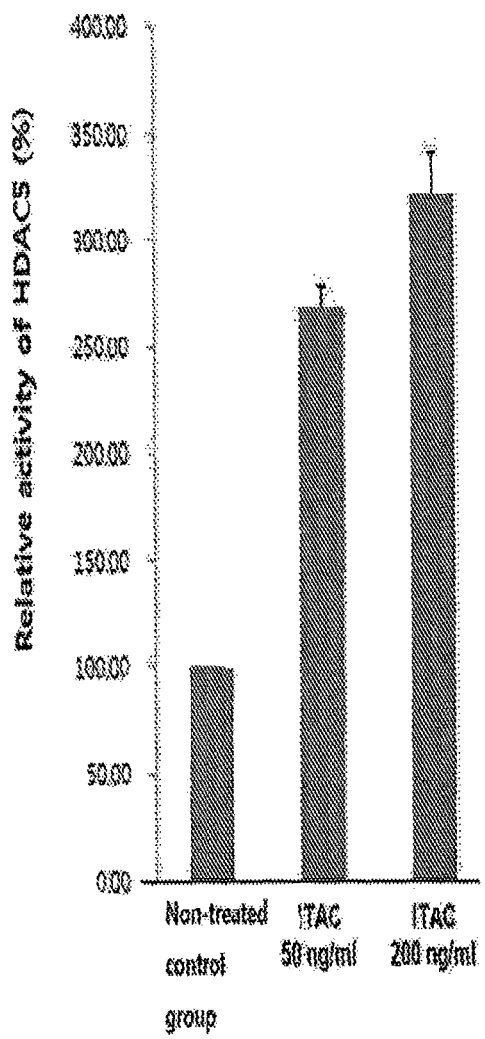

METHOD FOR SKIN WHITENING USING CHEMOKINE

CROSS REFERENCE TO RELATED APPLICATIONS

This application is a National Stage of International Application No. PCT/KR2015/007721 filed Jul. 24, 2015, claiming priority based on Korean Patent Application No. 10-2014-0098395, filed Jul. 31, 2014, the contents of all of which are incorporated herein by reference in their entirety.

TECHNICAL FIELD

The present invention relates to a composition containing a chemokine, particularly, an interferon-inducible T-cell alpha chemoattractant (ITACT) which can decrease the gene expression of a factor related to melanin pigment production in melanocytes, thereby exhibiting a skin whitening effect.

BACKGROUND ART

Melanocytes are present in the basal epidermis of skin, and play a role in producing a melanin pigment by external factors such as UV, transferring the produced melanin pigment to peripheral keratinocytes, thereby inhibiting DNA damage of the keratinocytes. However, the activity of these melanocytes is abnormally regulated by genetic factors, hormones and various disease factors, resulting in excessive pigmentation and hyperplasia beyond the normal level of pigment production, thereby leading to hyperpigmentation disorders such as freckles or lentigines or contributing as a factor for hypopigmentation disorders such as vitiligo.

The activation of excessive melanocytes is a state in which the homeostasis is lost in melanin pigment production due to chronic exposure of external stimuli such as ultraviolet rays. The skin is an elaborately regulated-immune system, and secretes a variety of cytokines, chemokines and other inflammatory mediators. The ultraviolet rays stimulate immune cells constituting the skin such as keratin-forming cells, macrophages, T cells and the like to induce the secretion of immune substances. Such immune substances not only create a chronic inflammatory state by accumulating immune cells to the microenvironment surrounding the periphery of the melanocytes, but also have an effect on the melanocytes themselves such as proliferation and migration of the melanocytes, and excessive production of melanin pigment.

Generally, it is well known that a cytokine, which is known as an immunological mediator, plays an important role in skin physiology such as atopic dermatitis and contact dermatitis, while a cytokine, which is an immunoreactive mediator with a small size of about 8 to 14 kD, shows a selective chemotaxis to surrounding cells, and has a function of inducing migration of cell and accumulation in a target organ, is not well known for its role in skin physiology. Similarly, studies on various immune substances have been conducted for an immuno-modulating therapy to regulate hyperpigmentation disorders caused by hyperactivation of melanocytes, but the direct influence of ITAC, which is a skin immune cell-derived factor and a chemokine, on melanocytes is not well known.

Immune responses caused by infections or internal or external injuries are well known for very precise control mechanisms. However, if a problem arises in the ability to precisely control the immune system, a chronic inflammation will occur, and such changes in the microenvironment will affect the activity of the surrounding cells.

Recently, it has been reported that the change in the cytokine mediating the immune response modifies the epigenetic pattern, thereby modifying the genes. And research on the treatment of chronic inflammation and further on the treatment of cancer caused by the the inflammation is actively carried out through epigenetic control substances. However, symptomatic genetic approaches to the melanocytes themselves or cells surrounding microenvironment regulation by the chemokine are a nonexistent state.

PRIOR ART DOCUMENT (Patent Document 1) Korean Patent Publication No. 10-2013-0056955 (Publication date: May 31, 2013)

DETAILED DESCRIPTION OF THE INVENTION

Technical Problem

The present inventors have made extensive effort to find out a method for regulating the activity of melanocytes or cells surrounding microenvironment through the regulation of the immune system, and as a result, they have discovered that the activation of melanocytes can be regulated by treating a chemokine, particularly ITAC, thereby completing the present invention.

Accordingly, one object of the present invention is to provide a composition which exhibits a skin whitening effect by regulating the activation of melanocytes by a chemokine.

Technical Solution

To achieve the above object, the present invention provides a skin whitening composition containing an interferon-inducible T-cell alpha chemoattractant.

ADVANTAGEOUS EFFECT

The composition of the present invention can provide a skin whitening effect by regulating the activation of melanocytes, and further is effective in alleviating and treating skin hyperpigmentation disorders such as freckles and lentigines.

BRIEF DESCRIPTION OF THE DRAWINGS

FIGS. 2A, 2B and 2C are graphs showing the result of an increase in gene expression, protein content and enzyme activity of HDAC5 in human melanocytes treated with ITAC.

DETAILED DESCRIPTION OF THE EMBODIMENTS

Figure 1A:
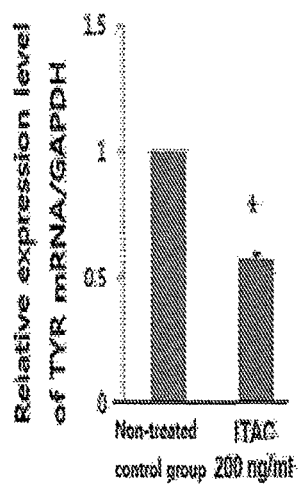
FIGS. 1A, 1B, 1C, 1D, 1E and 1F show graphs illustrating the result of a decrease in gene expression of factors related to melanin pigment production in human melanocytes treated with ITAC.
Figure 1B:
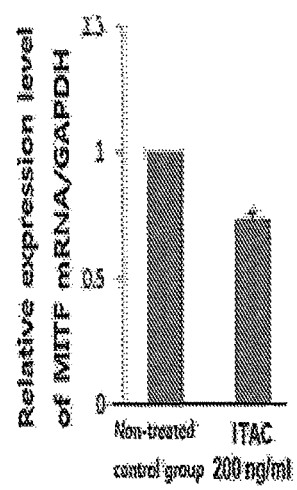
Figure 1C:
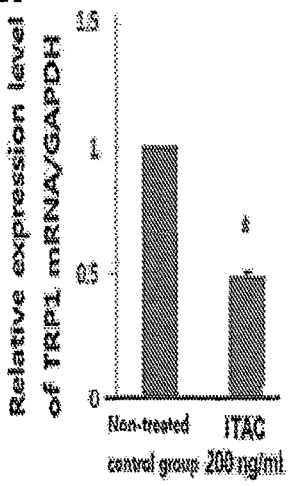
Figure 1D:
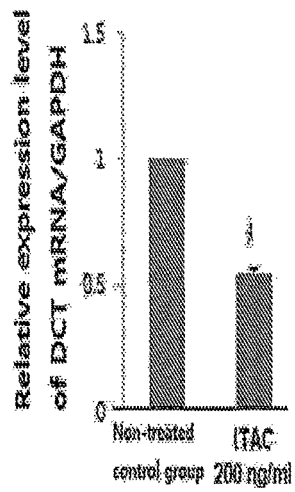
Figure 1E:
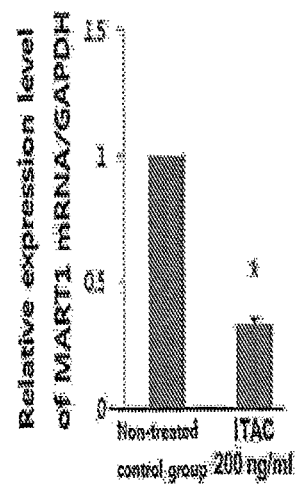
Figure 1F:
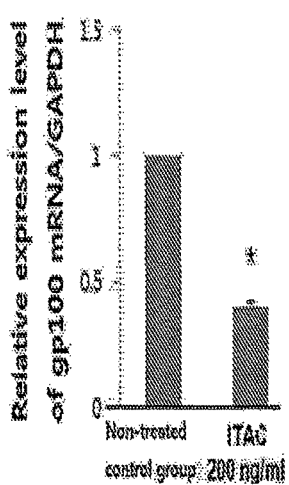

The present invention relates to a composition capable of providing a skin whitening effect by regulating the gene expression of the factors related to melanin pigment production by controlling the activation of melanocytes. The composition of the present invention contains, as an active ingredient, a chemokine, particularly an interferon-inducible T-cell alpha chemoattractant (ITAC; SEQ ID NO: 1).

The ITAC used in the present invention can be obtained from a number of suitable origins (e.g., human recombinant ITAC, Product No. 672-IT of R & D system). This can be produced by recombinant DNA methodology, for example by a method in which a gene encoding human ITAC is cloned and expressed in a host system, while permitting the production of large quantities of pure human ITAC. Biologically active building blocks or fragments of ITAC may also be used in the present invention.

The composition of the present invention contains ITAC as an active ingredient in an amount of 0.0001 to 0.0005% by weight based on the total weight of the composition. If ITAC is contained in an amount of less than 0.0001% by weight, it is not sufficient to inhibit the activity of tyrosinase for whitening of the skin, whereas if it is contained in an amount exceeding 0.0005% by weight, it is not suitable for containing and formulating other ingredients.

The composition according to the present invention provides an excellent skin whitening effect, and is also effective in alleviating and treating skin hyperpigmentation disorders such as symptoms of freckles or lentigines, and post-inflammatory pigmentation such as acne.

The composition according to the present invention is a composition for external skin application, and may be formulated into a conventional external preparation, a cosmetic formulation or a pharmaceutical formulation.

The composition according to the present invention may be formulated by containing a cosmetically or dermatologically acceptable medium or base. It may be provided in any form suitable for topical application, for example, in the form of solutions, gels, solids, paste anhydrous products, emulsions obtained by dispersing oil phase in aqueous phase, suspensions, microemulsions, microcapsules, microgranules or ionic (liposomes) and non-ionic vesicle dispersants, or in the form of creams, skins, lotions, powders, ointments, sprays or conceal stick. It may also be used in the form of a foam or an aerosol composition further containing a compressed propellant. These compositions may be prepared according to a conventional method in the art.

The cosmetic composition according to the present invention may contain adjuvants commonly used in cosmetic or dermatological science such as fatty substances, organic solvents, solubilizing agents, thickening agents, gelling agents, softening agents, antioxidants, suspending agents, stabilizing agents, foaming agents, flavoring agents, surfactants, water, ionic or non-ionic emulsifiers, fillers, sequestering agents, chelating agents, preservatives, vitamins, blockers, wetting agents, essential oils, dyes, pigments, hydrophilic or lipophilic active agents, lipid vesicles or any other ingredient commonly used in cosmetics. Such adjuvants are introduced in the amounts commonly used in the cosmetic or dermatological fields.

Further, the composition according to the present invention may be formulated as a pharmaceutical composition by further containing a suitable pharmaceutically acceptable carrier, excipient and diluent.

The pharmaceutical dosage form of the present invention is not particularly limited, but may be used alone or in combination with other pharmaceutically active compounds.

The pharmaceutical composition according to the present invention may be formulated into any form suitable for pharmaceutical preparations, in addition to transdermal dosage forms such as lotions, ointments, gels, creams, patches and sprays according to conventional methods.

The preferred dosage of the pharmaceutical composition of the present invention varies depending on the age, gender, weight, symptom, severity of disease, drug form, route and duration of administration of a subject, but can be appropriately selected by those skilled in the art. However, for a desired effect, the pharmaceutical composition of the present invention may be administered in the range of 1 mg/kg per day to 5000 mg/kg per day, but is not limited thereto. The administration may be performed once or multiple times a day. In addition, the dose may be increased or decreased according to the age, gender, weight, severity of disease, route of administration and the like. Accordingly, the dose does not, in any way, limit the scope of the invention.

Further, the composition of the present invention may contain a skin absorption promoting-substance to increase the skin whitening effect.

BEST MODE

Hereinbelow, the present invention will be described in detail by way of Examples and Test Examples. However, these Examples are given for illustrative purposes only, and the scope of the invention is not intended to be limited by these Examples. Further, modifications, substitutions and insertions, etc. conventionally known in the art can be made to the invention, without deviating from the scope of the present invention.

REFERENCE EXAMPLE 1

Preparation of Melanocytes

Human melanocytes purchased from Cascade (Normal Human Epidermal Melanocyte-Moderately pigmented, Product No. C-102-5C) were seeded into a 100 cm$^2$ plate in a number of 6×10$^5$ cells, 254 medium (Product No. M-254-500, Gibco) containing HMGS (Human Melanocyte Growth Supplement; Product No. S-002-5, Gibco) was used as a basal medium, and the cells were incubated at 37° C. in a 5% $CO_2$ incubator. When the density reached about 70 to 80%, the cells were subcultured, and the subcultured melanocytes were provided to the experiments carried out thereafter.

TEST EXAMPLE 1

Whether Gene Expression of Factors Related to Melanin Pigment Production in Human Melanocytes is Reduced by ITAC The human melanocytes were treated with ITAC to determine whether the pigment production of the melanocytes was reduced by ITAC. The Product No. 672-IT manufactured by R & D system was used for ITAC.

The human melanocytes cultured in Reference Example 1 above were treated with ITAC at a concentration of 200 ng/ml, and non-treated melanocytes were cultured at 37° C. and 5% $CO_2$ for 48 hours as a control group. The total mRNA of the cultured human melanocytes was extracted to synthesize cDNA, and Real-time PCR (Applied Biosystems, 7500 Fast) was performed using the synthesized cDNA.

The real-time PCR was carried out by repeating the cycle at 95° C. for 15 seconds and at 60° C. for 60 seconds for a total of 40 cycles. A relative value was measured as to how much the expression of the corresponding gene was increased compared to the gene expression of the control group, and the difference in relative gene expression between the samples was measured using tyrosinase (TYR), MITF, TYRP1, DCT, MART1 and gp100 primers, which are the typical melanin pigment production-stimulating factors. The primers were TaqMan primers manufactured by Applied Biosystems as follows: tyrosinase (TYR, Product No.: Hs01099965$_{13}$ ml), MITF (Product No.: Hs01117294$_{13}$ ml), TYRP1 (Product No.: Hs00167051$_{13}$ ml), DCT (Product No.: Hs01095856$_{13}$ ml), MART1 (Product No.: Hs00194133$_{13}$ ml), gp100 (PMEL, Product No.: Hs00173854$_{13}$ ml). The measurement results are shown in FIGS. 1A, 1B, 1C, 1D, 1E and 1F.

Based on the results shown in FIGS. 1A, 1B, 1C, 1D, 1E and 1F, it was confirm that the expression levels of the pigment production-stimulating factors were reduced by the treatment of ITAC and that the expression level of tyrosinase (TYR), TYRP1, DCT, MART1 and gp100 were significantly reduced. Based on this, it can be confirmed that ITAC has the ability to inhibit melanin pigment production by the mechanism.

TEST EXAMPLE 2

Increase in Expression Level and Enzyme Activity of HDAC5, a Histone Deacetylase, by ITAC The human melanocytes cultured in Reference Example 1 were treated with ITAC at a concentration of 50 ng/ml (Product No. 672-IT, R & D system) for 48 hours. cDNA was synthesized from the RNA isolated therefrom, and the change in mRNA level was measured by Q-PCR (Applied biosystems, 7500 Fast) using a primer of HDAC5 (histone deacetylase 5). The Q-PCR was carried out by repeating the cycle at 95° C. for 15 seconds and at 60° C. for 60 seconds for a total of 40 cycles, and a relative value was measured as to how much the expression of the corresponding gene was increased compared to the gene expression of the control group. The HDAC5 primer used in the experiment above was TaqMan primer (Product No. Hs00608366_m1) manufactured by Applied Biosystems.

Based on the measurement results shown in FIG. 2A, it can be confirmed that when 50 ng/ml of ITAC was treated, the expression level of HDAC5 mRNA was remarkably increased compared to the non-treated control group.

Further, the human melanocytes cultured in Reference Example 1 were treated with 50 ng/ml of ITAC (Product No. 672-IT, R & D system) for 48 hours. 30 μg of the cell lysate was loaded, and the level of protein expression of HDAC5 was confirmed by western blotting.

Based on the results shown in FIG. 2B, it was confirmed that although no change was observed in the expression of GAPDH which is a control group, the level of protein expression of HDAC5 was significantly increased when ITAC was treated.

Furthermore, in order to examine the effect of increasing the levels of mRNA and protein of HDAC5 by ITAC on enzyme activity, 50 ng/ml or 200 ng/ml of ITAC (Product No. 672-IT, R & D system) was treated to the human melanocytes cultured in Reference Example 1 above for 48 hours to prepare a cell lysate. The cell lysate was maintained at a low temperature until just before the experiment to maintain the enzyme activity. 10 μl of assistant reagent buffer(HDAC assay buffer) for HDAC analysis or 10 μl of assistant reagent buffer containing 4 μM of TSA (trichostatin A), which is a HDAC inhibitor and a control group, was aliquoted into a 96-well plate. After adding 20 μl of the cell lysate, the resultant was stored in an incubator at 37° C. for 10 minutes so that the maximum enzyme activity could be achieved.

Then, 10 μl of 4 mM substrate was added and reacted for 1 hour. 20 μl of an enzymatic activity amplification buffer (activator solution) was added and reacted at room temperature for 20 minutes, and the absorbance was measured at 405 nm (BioTek, Synergy 2). Here, the enzyme activity was quantitatively calculated as the activity (%) relative to the control group. On the other hand, in this experiment, it was concluded that when the enzyme activity of HDAC5 was inhibited by 70 to 100% in the experimental group containing TSA, which is a broad-spectrum HDAC inhibitor, this experiment was considered to work effectively, and the enzyme activity of HDAC5 was measured using the HDAC assay kit (17-374) manufactured by Upstate.

Based on the measurement results shown in FIG. 2C, it can be confirmed that ITAC increases the enzyme activity of HDAC5 in a concentration-dependent manner in the range of 50 to 200 ng/ml used in the present invention.

TEXT EXAMPLE 3

Inhibition of Melanin Pigment Production by HDAC5

The melanocytes, which excessively produce HDAC5 protein compared to the cells in control group using an HDAC5 overexpression vector, were centrifuged (Eppendorf, centrifuge 5415R, Germany), and the pellet was isolated therefrom and observed for color.

Figure 3A:
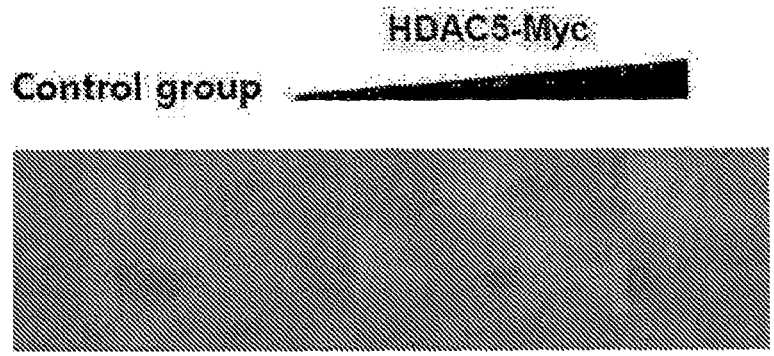
FIGS. 3A and 3B show illustrating the result of a decrease in melanin pigment production in human melanocytes into which an HDAC5 over-expression system is introduced.

As a result of comparing it with the non-treated group used as a control group, as shown in FIG. 3A, the overexpression of HDAC5 reduced the amount of melanin pigment production in a concentration-dependent manner.

The content of the pellet was dissolved with sodium hydroxide, and the absorbance was measured at OD490 which is specific for melanin pigment (BioTek, Synergy2) and corrected by the total protein content.

Figure 3B:
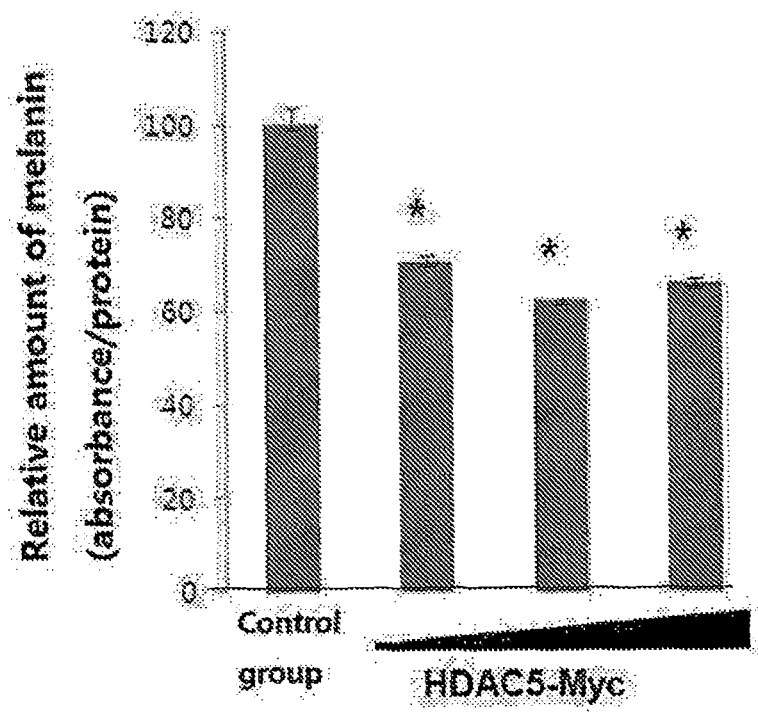

Based on the results shown in FIGS. 3A and 3B, it can be confirmed that the overexpression of HDAC5 induces a reduction in the amount of melanin in a concentration-dependent manner.

SEQUENCE LISTING FREE TEXT

SEQ ID No. 1 represents the sequence of ITAC.

The invention claimed is:

1. A method of whitening the skin of a subject in need thereof, the method comprising applying a composition, which contains an effective amount of interferon-inducible T-cell alpha chemoattractant comprising SEQ ID NO:1 as an active ingredient, to the skin.

2. The method as claimed in claim 1, wherein the composition inhibits the gene expression of a factor related to melanin pigment production in a melanin-forming cell.

3. The method as claimed in claim 1, wherein the composition increases the gene expression of histone deacetylase.

4. The method as claimed in claim 1, wherein the composition improves a condition of skin hyperpigmentation disorder.

5. The method as claimed in claim 4, wherein the condition of skin hyperpigmentation disorder is freckles or lentigines.

6. The method as claimed in claim 4, wherein the skin hyperpigmentation disorder is caused by post-inflammatory pigmentation.

7. The method as claimed in claim 1, wherein the composition is a cosmetic composition for external skin application.

* * * * *

SEQUENCE LISTING

```
<160> NUMBER OF SEQ ID NOS: 1

<210> SEQ ID NO 1
<211> LENGTH: 94
<212> TYPE: PRT
<213> ORGANISM: Artificial Sequence
```

```
<220> FEATURE:
<223> OTHER INFORMATION: Interferon-inducible T-cell alpha
      chemoattractant

<400> SEQUENCE: 1

Met Ser Val Lys Gly Met Ala Ile Ala Leu Ala Val Ile Leu Cys Ala
 1               5                  10                  15

Thr Val Val Gln Gly Phe Pro Met Phe Lys Arg Gly Arg Cys Leu Cys
                20                  25                  30

Ile Gly Pro Gly Val Lys Ala Val Lys Val Ala Asp Ile Glu Lys Ala
            35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```